United States Patent
Hölzl

(10) Patent No.: US 6,566,871 B2
(45) Date of Patent: May 20, 2003

(54) PROCESS AND DEVICE FOR TESTING A WORKPIECE BY MEANS OF EDDY CURRENTS

(75) Inventor: Roland Hölzl, München (DE)

(73) Assignee: Pruftechnik Dieter Busch AG, Ismaning (DE)

( * ) Notice: Subject to any disclaimer, the term of this patent is extended or adjusted under 35 U.S.C. 154(b) by 0 days.

(21) Appl. No.: 09/953,245

(22) Filed: Sep. 17, 2001

(65) Prior Publication Data
US 2002/0074996 A1 Jun. 20, 2002

(30) Foreign Application Priority Data
Sep. 15, 2000 (DE) .......................... 100 45 715

(51) Int. Cl.⁷ ............................................. G01N 27/90
(52) U.S. Cl. ....................... 324/240; 324/238; 324/225; 702/38
(58) Field of Search ................ 324/237, 238, 324/239, 240, 220, 228, 242; 702/38

(56) References Cited

U.S. PATENT DOCUMENTS

| | | | |
|---|---|---|---|
| 4,064,452 A | * 12/1977 | Toth ........................... 324/202 |
| 4,355,281 A | 10/1982 | Toth et al. |
| 4,488,114 A | * 12/1984 | David et al. ................. 324/225 |
| 4,629,985 A | * 12/1986 | Papadimitriou et al. .... 324/227 |
| 4,646,013 A | 2/1987 | Törnblom |
| 4,763,274 A | * 8/1988 | Junker et al. ............... 324/220 |
| 4,799,011 A | 1/1989 | Muller |
| 4,853,634 A | 8/1989 | Törnblom |
| 5,339,256 A | * 8/1994 | Levy et al. .................. 702/38 |
| 5,371,462 A | 12/1994 | Hedengren et al. |
| 5,602,474 A | 2/1997 | Morrey, Jr. |
| 5,737,445 A | * 4/1998 | Oppenlander et al. ...... 324/238 |
| 5,898,304 A | 4/1999 | Mandl |
| 6,037,768 A | * 3/2000 | Moulder et al. ............. 324/202 |
| 6,424,151 B2 | * 7/2002 | Kawata et al. ............... 324/220 |

FOREIGN PATENT DOCUMENTS

| EP | 0 282 930 A2 | 9/1988 | |
| JP | 410300725 A | * 11/1998 | ........ G01N/27/90 |

OTHER PUBLICATIONS

Sikora et al., "Artificial Neural Network Application for material evaluation by electromagnetic methods," International Joint Conference on Neural Networks, 1999, vol. 6, pp. 4027–4032.*
Zhang et al. "A New Fuzzy Neural Network Architecture for Multisensor Data Fusion in Non–Destructive Testing," IEEE International Fuzzy Systems Conference Proceedings, Aug. 22–25, 1999, Seoul, South Korea, pp. 1661–1665.*
Conjugate Spectrum Filters for Eddy Current Signal Processing Tadeusz Stepinski et al., Materials Evaluation, vol. 51, No. 7, Jul. 1993, pp. 839–844.
Analysis of Eddy Current Patterns, T. Stepinski, British Journal of NDT, vol. 32, No. 12, Dec. 1990, pp. 631–633.

* cited by examiner

Primary Examiner—Edward Lefkowitz
Assistant Examiner—Darrell Kinder
(74) Attorney, Agent, or Firm—Nixon Peabody LLP; David S. Safran

(57) ABSTRACT

The invention relates to a process for testing of a workpiece by means of eddy currents induced by a field coil in the workpiece and from which a measurement signal is obtained by means of a measurement sensor, a pattern signal representative of a workpiece fault being generated, a correlation function of the measurement signal acquired by the sensor with the pattern signal being determined, and the correlation function being evaluated in order to detect a fault in the workpiece. The invention furthermore relates to a device for executing the process.

22 Claims, 6 Drawing Sheets

PROCESS AND DEVICE FOR TESTING A WORKPIECE BY MEANS OF EDDY CURRENTS

BACKGROUND OF THE INVENTION

1. Field of the Invention

This invention relates to a process and a device for testing of a workpiece by means of eddy currents which are induced by a field coil in the workpiece and from which a measurement signal is obtained by means of a measurement sensor.

2. Description of Related Art

Testing of an electrically conductive workpiece by means of eddy currents relies upon the fact that material faults in the workpiece or test piece (for example, cracks, voids, surface damage, poor welds, etc.) hinder the propagation of eddy currents which are induced by means of the field coil; this acts on the electromagnetic field which has been formed in turn by the eddy currents. This electromagnetic field which has been produced by the eddy currents is measured by means of a sensor which can be a field coil itself or at least one separate measurement coil. If there is only a single separate measurement coil, this arrangement is called an "absolute coil". Two or more measurement coils can be connected in a subtractive manner; this is called a "difference coil" and enables for example a temperature drift to be excluded. A material fault which influences the eddy currents can thus be considered an impedance change of the measurement coil which is coupled to the test piece, the fault signals being conventionally displayed as a vector quantity (amplitude and phase angle) in the impedance plane of the measurement coil. The phase shift of the eddy currents with respect to the exciter voltage depends among other things on the thickness of the material. The exciter frequency determines the penetration depth and the phase shift of the eddy currents in a certain material depth.

Examples of phase-selective evaluation of eddy current measurements for material testing can be found for example in published European Patent Application No. 0 282 930, and in U.S. Pat. Nos. 4,646,013, 4,355,281, 4,853,634, and 5,371,462 discloses eliminating measurement signals which originate not from faults, but from the effects of the geometry of the test piece, for example edges, by generating a reference background signal by scanning a fault-free workpiece identical to the test specimen, which signal is withdrawn from the measurement signal obtained for the test specimen after the actual measurement of the latter.

Basically, the evaluation of the eddy current signals can be prevented or hindered by noise signals (this includes generally interference signals of all types which can also be periodic) which can be produced by mechanical or electromagnetic interference (for example, by a welding machine in the line). In addition, the surface of the test specimen can lead to increased background noise when it is for example a galvanized surface. In practice, the attempt has been made to counter these difficulties by modification of the exciter frequency, multi-frequency processes, or modification of the filters. However, it has been shown that existing measurement and evaluation processes do not always lead to sufficiently reliable and reproducible results. In particular, it would be desirable to detect fault signals in the vicinity of or below the noise level as well.

SUMMARY OF THE INVENTION

An object of this invention is to devise a process and a device for testing a workpiece by means of eddy currents in which faults can be detected with greater reliability and accuracy than in the known methods.

This object is achieved by a process and a device as disclosed hereinafter. It is advantageous that the reliability of fault detection can be greatly increased principally for very noisy measurement signals by evaluating the correlation of the measurement signal to a pattern signal representative or typical of a workpiece fault instead of the actual measurement signal.

DETAILED DESCRIPTION OF THE INVENTION

Figure 6:
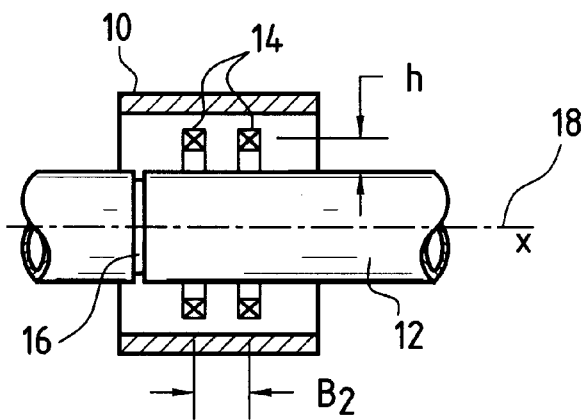
FIG. 6 illustrates one possible measurement arrangement.

FIG. 6 schematically shows one measurement arrangement for testing a workpiece by means of eddy currents, in which a field coil 10, supplied with an AC voltage of a certain frequency, induces eddy currents in an electrically conductive pipe 12 which is surrounded by the field coil 10. Furthermore, there are two measurement coils 14 which are located within the field coil 10 and which likewise surround the pipe 12. The measurement coils 14 are connected as a difference coil so that only one fault signal can appear when the voltages which have been generated via the eddy currents in the pipe 12 are different on the two coils 14. A fault on the pipe 12 is labelled with the reference number 16, and is shown as being an annular groove. The pipe 12 is moved by means of a drive parallel to the coil axes in the direction of the arrow 18.

The measurement arrangement shown in FIG. 6 can be identified by a characteristic quantity which is called the "effective coil width" (see DIN 54141) and which depends on the air gap h between the measurement coils 14 and the outside circumference of the pipe 12, the coil base $B_s$, the exciter frequency and the electrical conductivity, the diameter and the wall thickness of the pipe 12. The effective coil width can be determined for a stipulated measurement arrangement by measurement on a comparison pipe from tables or diagrams which are supplied by the coil manufacturer or by using reduced data from the coil manufacturer by means of known approximation formulas.

Figure 1A:
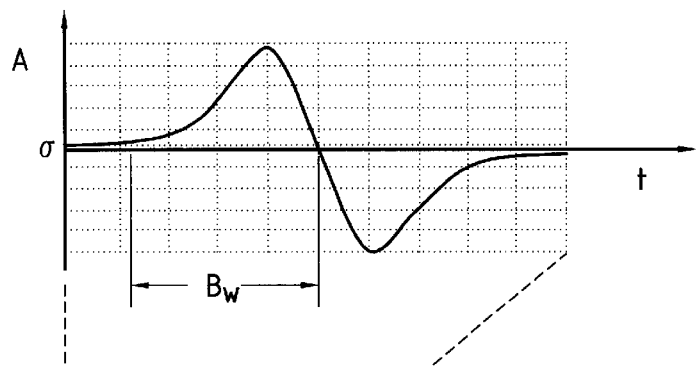
FIGS. 1A to 1C illustrate, by way of example, a pattern signal, a measurement signal, and their cross correlation, respectively.

FIG. 1A shows, by way of example, a measurement signal which is obtained by a difference coil arrangement like the one shown in FIG. 6 when there is a fault which is small compared to the coil extension. The effective coil width $B_w$ which is characteristic of the given measurement arrangement is likewise shown in FIG. 1A. In the example, the signal amplitude, i.e. the difference signal between the two measurement coils 14, is plotted as a function of the time, i.e. the position of the test specimen.

If the effective coil width is known it is possible to theoretically determine the time behavior of a fault signal by means of approximation for example by a simple Dirac pulse or a differentiated Dirac pulse. FIG. 1A shows one such signal behavior over time caused by a fault; hereinafter this is called the "pattern signal".

Alternatively to the described theoretical determination of the pattern signal from the effective coil width it is also possible to determine the pattern signal directly from a reference measurement on a test piece with a defined fault. It goes without saying that the reference test specimen should be identical to the test specimen which is actually being tested, aside from the defined fault; this also applies to the measurement conditions, especially the exciter frequency and the air gap. However, if identical test conditions cannot be produced, a "conversion" of the measured reference signal to the measurement conditions for the test specimen to be tested can be done from the known relationships between the effective coil width and the measurement parameters, when the latter are known, in order to determine the pattern signal.

Figure 1B:
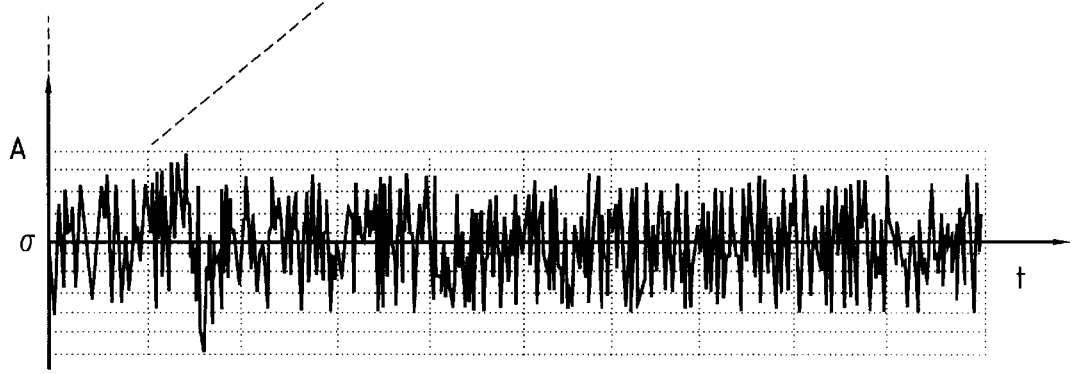

FIG. 1B shows, by way of example, a noisy measurement signal which was produced by white noise being superimposed on the pattern signal from FIG. 1A by means of a numerical noise generator (the time scale is stretched here in FIG. 1A compared to FIG. 1B, as shown by the drawing). It is apparent that by means of conventional eddy current signal evaluation the pattern signal, i.e., the fault signal, could not be reliably detected since it hardly rises above the noise. Reliable fault detection would therefore not be possible for the measurement signal from FIG. 1B by means of conventional evaluation.

Figure 1C:
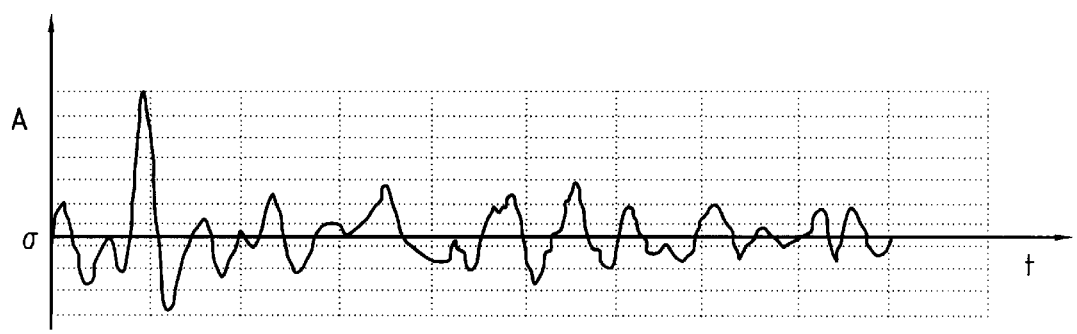

FIG. 1C shows (with the same time scale as FIG. 1B) the cross correlation function which was obtained by subjecting the pattern signal from FIG. 1A to a cross correlation with the noisy measurement signal from FIG. 1B. Here, it is apparent that in the cross correlation function from FIG. 1C the simulated fault clearly rises above the noise, while this is not the case in the actual measurement signal as shown in FIG. 1B. The reliability of signal evaluation can thus be greatly improved by the cross correlation of the noisy measurement signal with a fault pattern signal which is representative of the measurement conditions used.

Figure 2A:
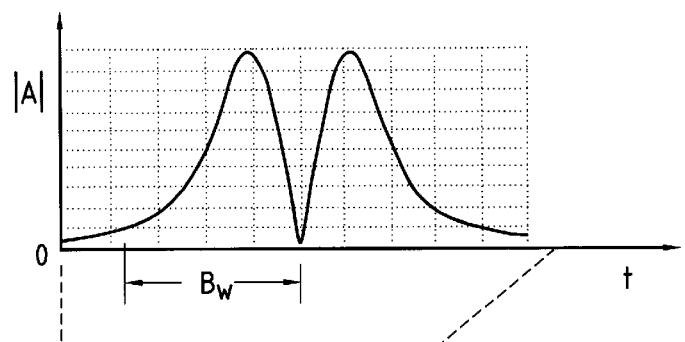
FIGS. 2A to 2C, corresponding to FIGS. 1A to 1C, illustrates the corresponding absolute value signals being plotted and the measurement signal having been evaluated as shown in FIG. 2B with quadrature.
Figure 2B:
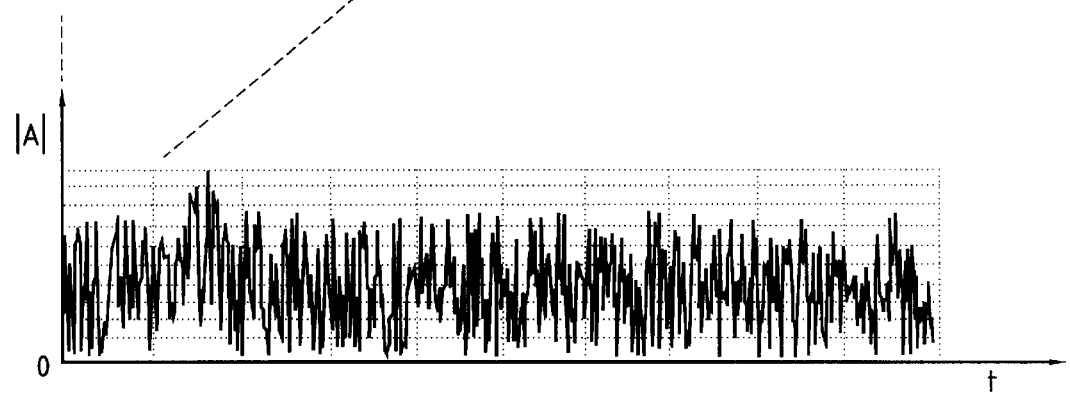
Figure 2C:
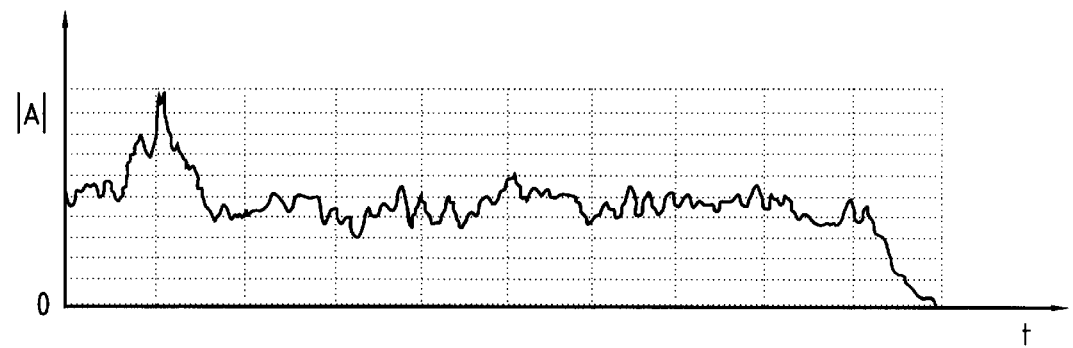

FIG. 2A shows the absolute value of the signal from FIG. 1A; FIG. 2B shows the absolute value measurement signal from FIG. 1B which has been quadrature-weighted and FIG. 2C shows the corresponding cross correlation function. Here too, it is apparent that the cross correlation with the pattern signal can considerably increase the reliability of fault detection. In both cases, a signal/noise ratio of 6 dB tends to be attainable; however, in both cases, due to the lack of reproducibility, direct evaluation of the noisy measurement signals would not make sense, but rather an evaluation of the measurement signals which have been correlated with the pattern signal.

In this invention, what is decisive is simply that a correlation function between the measurement signal and a representative pattern signal is undertaken and then instead of the measurement signal the correlated signal or the correlation function is evaluated. How the correlation function is determined in detail depends on the special circumstances. Thus, fundamentally, instead of determining the cross correlation function as shown in FIGS. 1 and 2, the determination of the correlation function can be done for example by using a neural network. Any process is suitable which is able to detect or quantify the presence of a stipulated pattern signal in a noisy signal.

Basically, determination and evaluation of the pattern signal or measurement signal can be done in the frequency domain instead of in the time domain, as shown.

Figure 4:
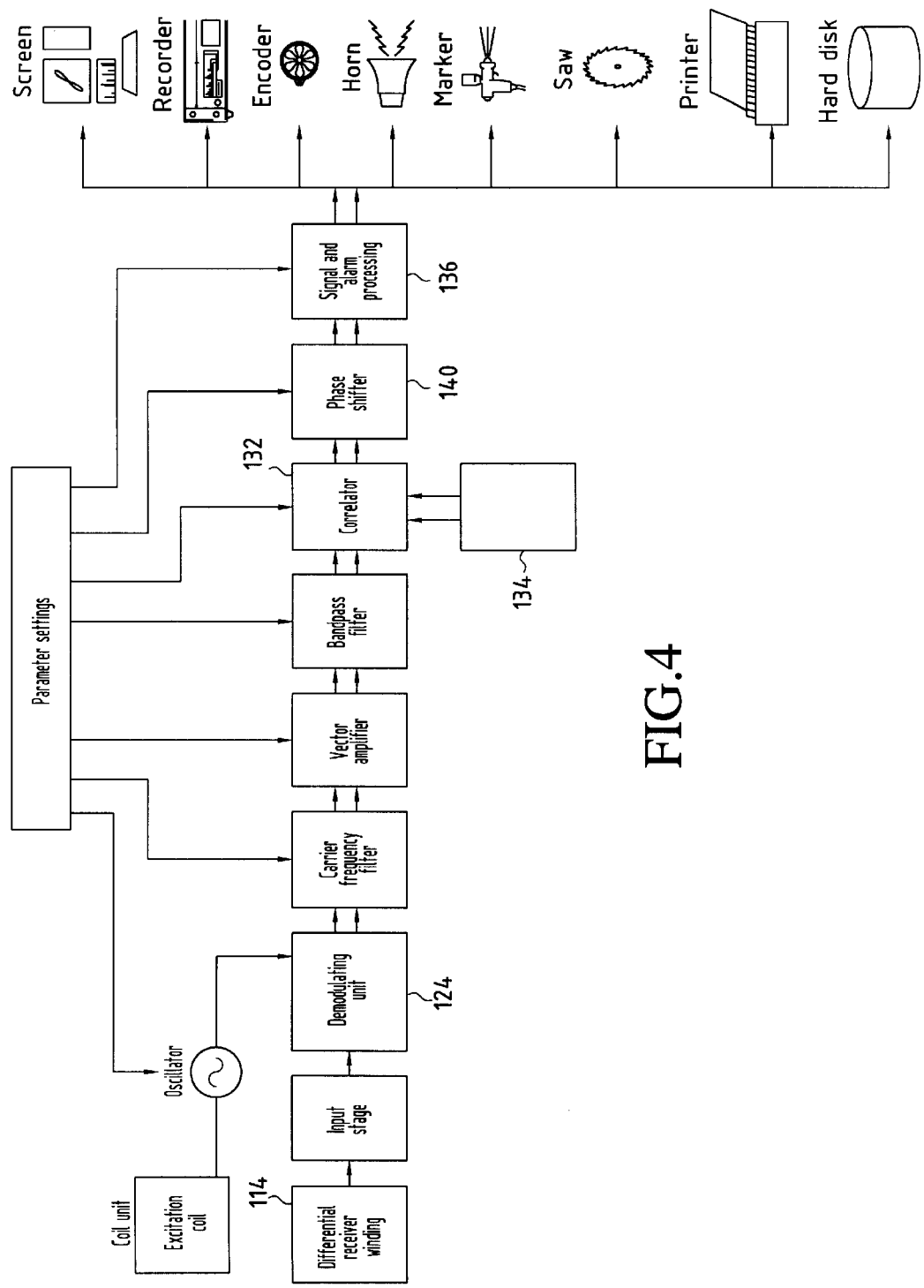
FIG. 4 shows a view, like FIG. 3, according to a second embodiment.

Evaluation of the determined correlation function can take place in the conventional manner like evaluation of the actual measurement signal in the known processes. It is evident that the signals shown in FIGS. 1 and 2 represent signals which have been demodulated with respect to the exciter frequency. Basically pure amplitude modulation can take place, as is the case in the signals shown in FIG. 2, i.e., there is no phase-selective demodulation, or the measurement signal can be demodulated in a phase-sensitive manner, this then taking place preferably in two channels with a phase shift of 90°. In this case, then each of the two channels is correlated with its own pattern signal, the evaluation of the fault signal with respect to amplitude and phase taking place from the two correlation functions which have been formed in this way, as illustrated in FIG. 4.

Preferably, determination and evaluation of the correlation function take place in real time. The correlation function can be basically correlated in addition to or alternatively to the conventional evaluation of the actual measurement signal. In doing so, the evaluation of the correlation function can be limited to detection of a fault near and below the noise level of the measurement signal, while for evaluation of faults above the noise level the conventional evaluation of the measurement signal is used. However, for control purposes an additional evaluation of the correlation function can also be done for faults above the noise level of the measurement signal.

Figure 3:
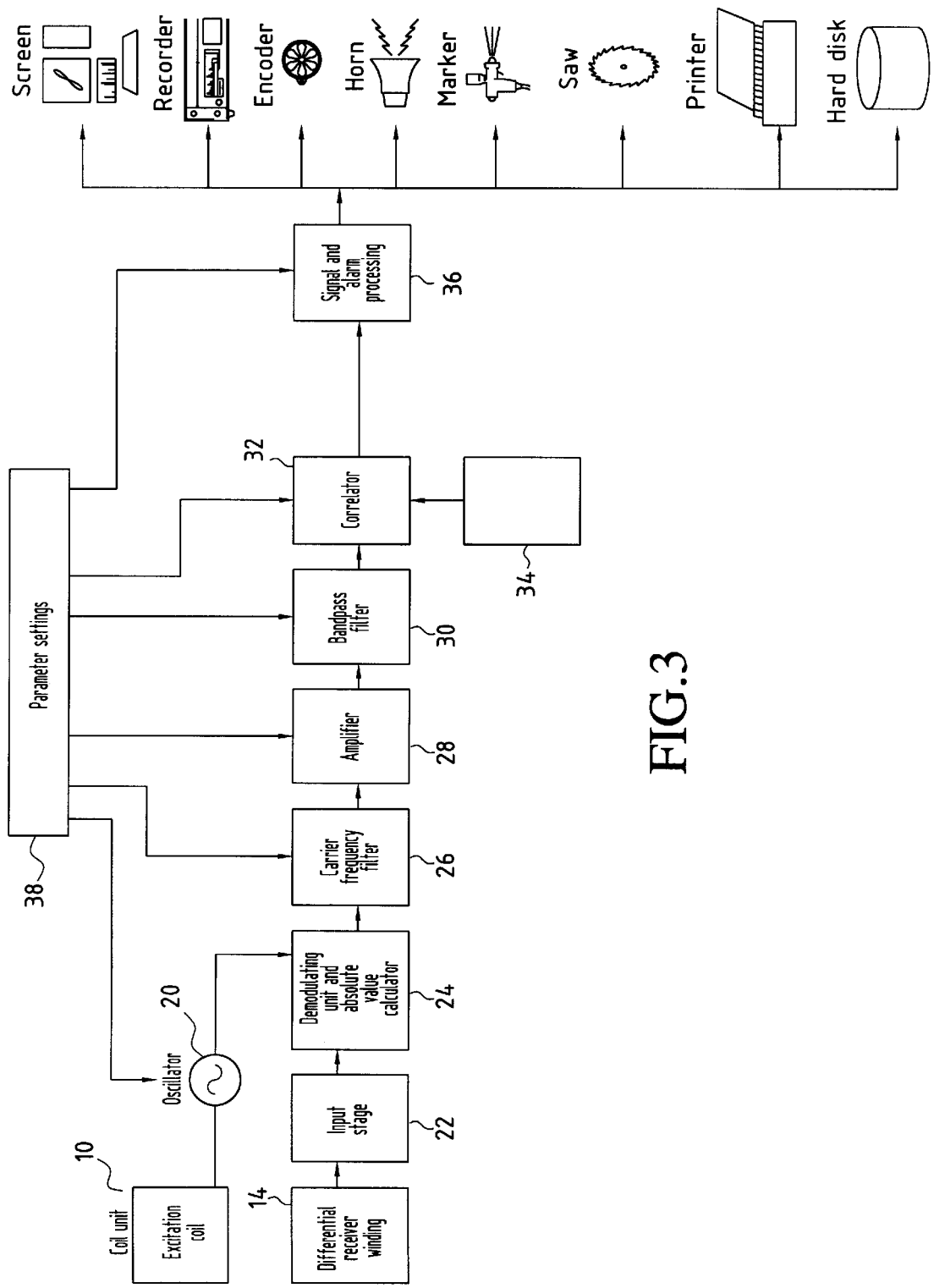
FIG. 3 schematically shows a device of the invention for eddy current testing according to a first embodiment.

FIG. 3 schematically shows the structure and manner of operation of a means for material testing by means of eddy currents. The field coil 10 is supplied by an oscillator 20 with an AC voltage of a desired frequency in order to induce eddy currents in a test specimen which in turn induce a voltage in the difference coil arrangement 14. The voltage signal tapped at the difference coil arrangement 14 is supplied, via an input stage 22 with a preamplifier which can also be frequency-selective depending on the type of modulation process, to a unit 24 in which demodulation with respect to the exciter frequency of the oscillator 20 and absolute value formation take place. The demodulated absolute value signal is routed through a filter 26 which filters the carrier frequency components out of the signal. The signal which has been filtered in this way is amplified by means of an amplifier 28 and routed through a preferably variable bandpass filter 30 which filters out interference which is superimposed on the signal and which may be present, especially at higher frequency interference. The measurement signal which has been filtered in this way is supplied to a correlator unit 32 in which the cross correlation function between the measurement signal and the pattern signal which has been prepared by the unit 34 is determined. The pattern signal can be produced in the manner described above using the effective coil width.

The correlation function which was produced in the correlator unit 32 is supplied to a signal processing unit 36 which evaluates the correlation function and optionally determines the presence of a fault. The evaluated signal is displayed on a screen and recorder and can furthermore be output on a printer and stored in a storage medium. If the signal processing unit 36 decides on the presence of a fault, an acoustic and/or optical alarm is triggered, the faulty site of the test specimen being provided with a color marking or a notch.

A rotary transducer can be provided to determine the actual speed of the line, i.e. the speed of the test specimen so that, for example, positionally-accurate marking of the test specimen is enabled, with a length which can be recorded in the report and filters with frequencies can be changed depending on the line speed.

The oscillator 20, the amplifier 28, the correlator unit 32, the signal processing unit 36 and the filters 26 and 30 are controlled by a control unit 38.

Since in this case absolute value formation of the measurement signal and accordingly also absolute value formation of the pattern signal are done, only the signal amplitude can be evaluated without phase information in fault detection.

FIG. 4 shows an eddy current test means similar to FIG. 3, in which rather than the absolute value signals, the component signals are determined and evaluated so that in this case the phase information of the measurement signal can be taken into account at the same time in fault detection. In the demodulation unit 124, no absolute value formation takes place, but rather phase-sensitive, two-channel demodulation with a phase displacement of 90° between the two channels is carried out (for example, by means of phase-controlled rectifiers), i.e., phase-synchronous demodulation of the measurement signal with the sine and cosine of the exciter signal takes place. This two-channel demodulation into component signals necessitates the signal path between the demodulation unit 124 and the signal processing unit 136 being made two-channel. Consequently the carrier frequency filter 126, the amplifier 128 (which in this case is made as a vector amplifier) and the bandpass filter 130 are made two-channel. The correlator 132 is made two-channel, for each measurement signal channel, i.e., both for the sine component and also the cosine component, its own correlation function is determined. In doing so, for each channel the unit 134 prepares its own pattern signal. The determined correlation functions pass through a phase shifter 140 which makes it possible to adjust the phase angle of the fault signal in a manner which is favorable for evaluation before they are sent to the signal processing unit 136 which in the conventional manner determines the amplitude and the phase angle of the fault signal from the two determined correlation functions. As a result, for each potential fault signal, then a fault signal is obtained which has a length which indicates the signal amplitude and its direction indicates the phase angle of the fault signal, by which the fault can be displayed on the screen in the complex impedance plane of the difference coil 114.

Figure 7:
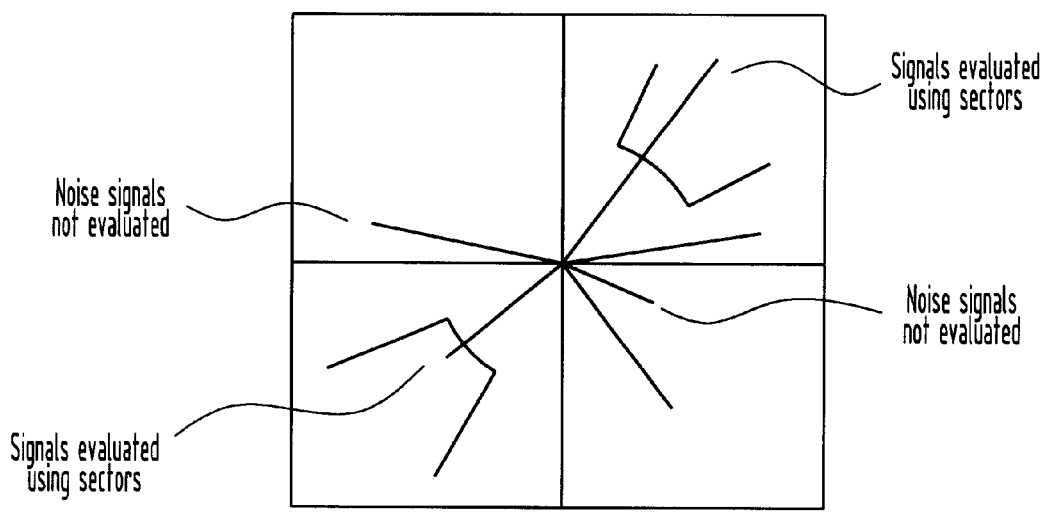
FIG. 7 illustrates one example for evaluation of fault signals by means of delta vector formation.

With reference to the signal evaluation, it should be noted that in a pure amplitude evaluation as shown in FIG. 3 this is done feasibly by stipulating certain threshold values so that, for example, signals with an overly small or overly large amplitude are not identified as faults. In the phase-sensitive component signal evaluation as shown in FIG. 4, in addition to those amplitude threshold values phase threshold values can also be stipulated within which there must be a signal in order to be identified as faults. In this case certain sectors are obtained within which the determined fault vector must lie. This is shown in FIG. 7. The display of the signals as vectors in the complex impedance plane is especially graphic and efficient. The fault vectors (which are also called delta vectors) are computed as the vector between the extreme values of the phase-dependent amplitude.

In the phase-sensitive evaluation as shown in FIG. 4, the cost for correlation determination is roughly twice as great as for the pure absolute value evaluation as shown in FIG. 3, but due to the additionally obtained phase information a more complex evaluation of fault signals is possible, this can also be important for differentiation of various fault types. It should be noted that the correlator unit 132 with positive correlation delivers only positive signals so that without phase rotation sector evaluations make sense only in the first quadrant of the complex plane.

Basically it is also possible to carry out an evaluation by means of fuzzy logic in the signal evaluation in place of "sharp" thresholds.

Furthermore, it is also possible, as already mentioned above, before correlation of the measurement signal with the pattern signal to carry out a transformation into the frequency domain or into the frequency plane, i.e. typical frequency behaviors in the measurement signal are sought in the correlation.

The computer capacity necessary for signal correlation can also be used to ascertain the possible periodicity of the ascertained fault types; under certain circumstances this allows useful conclusions regarding for example qualitative shortcomings of rollers, especially in certain rollers, in the production of the test specimen and thus also the actual cause of the fault inside or outside of the production line.

Figure 5:
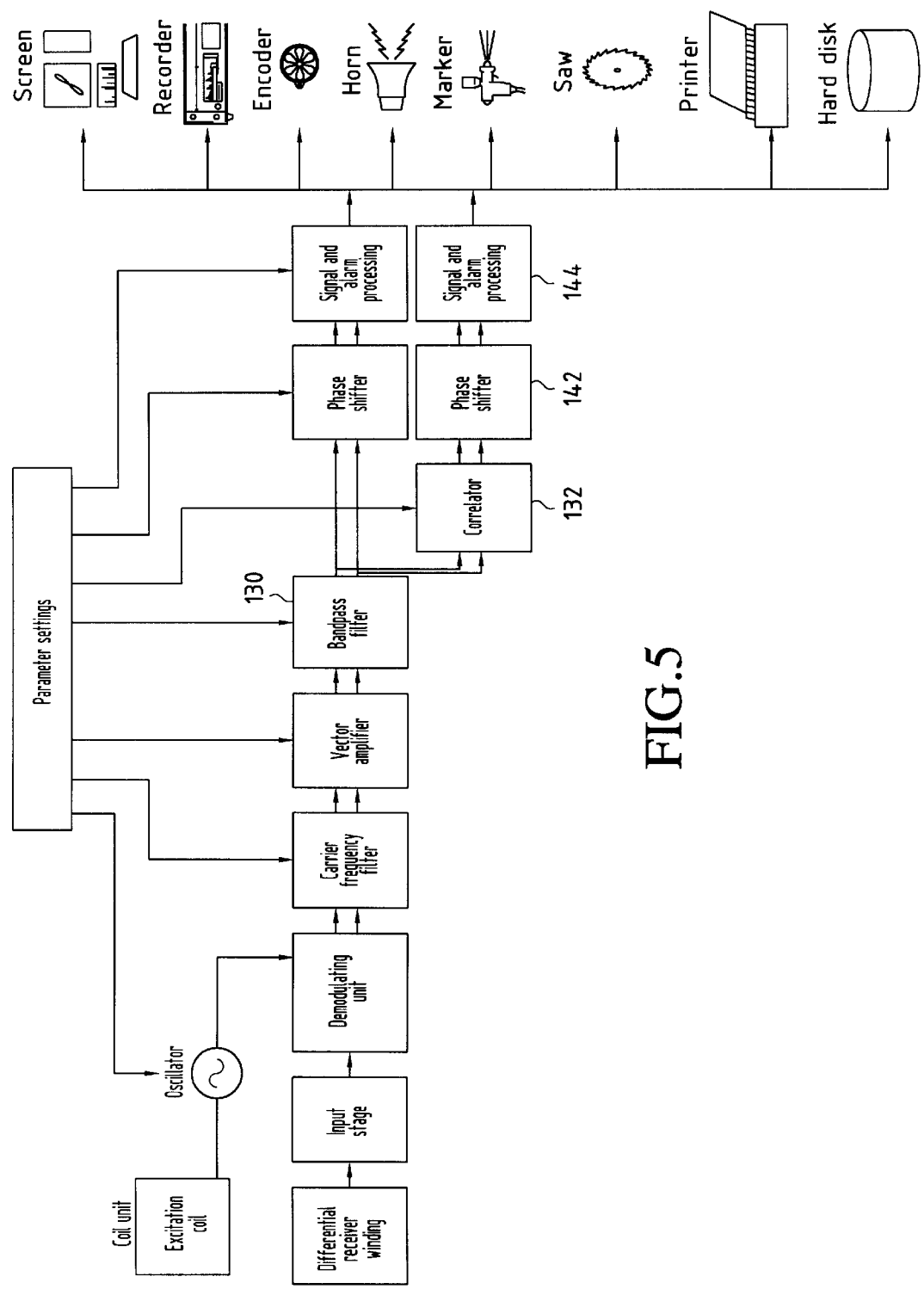
FIG. 5 shows a view, like FIG. 3, according to a third embodiment.

FIG. 5 shows a similar phase-sensitive eddy current test means as FIG. 4, but in addition to the evaluation of the signal correlated with the pattern signal, direct evaluation of the two channels supplied to the correlation unit 132 with the demodulated, amplified and filtered measurement signal takes place. For this purpose, the two measurement signal channels following the bandpass filter 130 are supplied not only to the correlation unit 132, but also to a second phase shifter 142 and after passing through it to a second signal processing unit 144. The signal evaluation thus takes place in four channels overall. This parallel evaluation of the actual measurement signal and of the measurement signal which has been correlated with the pattern signal at least for fault signals which are above the noise level enables use of signal information which is as complete as possible. In the area of the noise level or below, however, generally only evaluation of the measurement signal which has been correlated with the pattern signal will make sense. In this way the conventional direct evaluation of the measurement signal and the evaluation of the measurement signal correlated with the pattern signal can complement one another in order to enable determination of even relatively weak-signal faults in as reliable and reproducible manner as possible.

What is claimed is:

1. Process for testing of a workpiece through the use of eddy currents induced by a field coil in the workpiece and from which a measurement signal is obtained by means of a measurement sensor, comprising the steps of:

generating a pattern signal representative of a workpiece fault, determining a cross correlation function from the measurement signal acquired by the sensor and the pattern signal, and evaluating the cross correlation function in order to detect a fault in the workpiece.

2. Process as set forth in claim 1, wherein the pattern signal is determined by determining a characteristic value which characterizes the sensor depending on parameters which describe the measurement, and by computing the pattern signal for the workpiece fault as a function of the characteristic value using a model.

3. Process as set forth in claim 2, wherein the pattern signal is determined by approximation by means of a simple or differentiated Dirac pulse.

4. Process as set forth in claim 1, wherein the pattern signal is determined by a reference measurement on a workpiece with a defined fault.

5. Process as set forth in claim 2, wherein the sensor is a difference coil arrangement or absolute coil arrangement and a characteristic value is the effective coil width.

6. Process as set forth in claim 1, wherein determination of the cross correlation function takes place by means of a neural network.

7. Process as set forth in claim 1, wherein the pattern signal and the measurement signal are determined and correlated in the time domain.

8. Process as set forth in claim 1, wherein the pattern signal and the measurement signal are determined and correlated in the frequency domain.

9. Process as set forth in claim 1, wherein the pattern signal and the measurement signal are determined and correlated as absolute value signals without phase information.

10. Process as set forth in claim 1, wherein the pattern signal and the measurement signal are determined and correlated as component signals with phase information.

11. Process set forth in claim 1, wherein the measurement signal is demodulated before determining the cross correlation function.

12. Process set forth in claim 1, wherein, before determining the cross correlation function, the measurement signal is weighted.

13. Process as set forth in claim 12, wherein quadratic weighting is performed.

14. Process set forth in claim 1, wherein in addition to the cross correlation function the measurement signal itself is also evaluated for fault detection in the workpiece.

15. Process as set forth in claim 14, wherein the cross correlation function is used only to detect faults near and below the noise level of the measurement signal.

16. Process as set forth in claim 1, wherein the cross correlation function is used to detect faults above the noise level of the measurement signal.

17. Process as set forth in claim 1, wherein the workpiece is moved continuously past the sensor and the cross correlation function is determined and evaluated in real time.

18. Process as set forth in claim 10, wherein the measurement signal is demodulated in a phase-sensitive manner in two channels with a shift of 90 degrees and each of the two channels is correlated with its own pattern functions, the amplitude and phase of a fault signal being determined from the cross correlation functions which have been formed in this manner.

19. Process as set forth in claim 18, wherein the fault signal is evaluated by forming phase threshold values and amplitude threshold values.

20. Process as set forth in claim 19, wherein the amplitude and phase of the fault signal are displayed as a vector.

21. Process as set forth in claim 19, wherein evaluation takes place by means of fuzzy logic without using sharp threshold values for phase and amplitude.

22. Device for testing of a workpiece through use of eddy currents comprising, a field coil for inducing eddy currents in the workpiece, a measurement sensor for obtaining a measurement signal from the eddy currents induced in the workpiece, a means for producing a pattern signal representative of a workpiece fault, a correlator unit for determining the cross correlation function between the measurement signal, acquired by the sensor, and the pattern signal, and a unit for evaluating the cross correlation function in order to detect a fault in the workpiece.

\* \* \* \* \*